(12) United States Patent
Aoun et al.

(10) Patent No.: US 10,375,996 B2
(45) Date of Patent: Aug. 13, 2019

(54) INHALATOR AND CARTRIDGE THEREOF

(71) Applicant: British American Tobacco (Investments) Limited, London (GB)

(72) Inventors: Walid Abi Aoun, London (GB); Oleg Jurievich Abramov, St. Petersburg (RU); Gary Nicholson, London (GB); Pavel Fimin, St. Petersburg (RU); Helena Digard, London (GB)

(73) Assignee: British American Tobacco (Investments) Limited, London (GB)

( * ) Notice: Subject to any disclaimer, the term of this patent is extended or adjusted under 35 U.S.C. 154(b) by 158 days.

(21) Appl. No.: 15/521,082

(22) PCT Filed: Oct. 21, 2015

(86) PCT No.: PCT/EP2015/074395
§ 371 (c)(1),
(2) Date: Apr. 21, 2017

(87) PCT Pub. No.: WO2016/062777
PCT Pub. Date: Apr. 28, 2016

(65) Prior Publication Data
US 2017/0347706 A1  Dec. 7, 2017

(30) Foreign Application Priority Data
Oct. 22, 2014  (GB) .................................. 1418817.1

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 11/045* (2014.02);
(Continued)

(58) Field of Classification Search
CPC ..................................................... A24F 47/008
See application file for complete search history.

(56) References Cited

U.S. PATENT DOCUMENTS

| 4,756,318 A | 7/1988 | Clearman |
| 4,913,169 A | 4/1990 | Templeton |

(Continued)

FOREIGN PATENT DOCUMENTS

| AT | 507187 A4 | 3/2010 |
| CA | 885796 | 11/1971 |

(Continued)

OTHER PUBLICATIONS

Australian Examination Report, Application No. 2015334902, dated Dec. 22, 2017, 3 pages.

(Continued)

*Primary Examiner* — James Harvey
(74) *Attorney, Agent, or Firm* — Patterson Thuente Pedersen, P.A.

(57) ABSTRACT

In one aspect, apparatus is provided for generating an inhalable medium. The apparatus has a container for holding a liquid and a heater for volatilizing liquid held in the container. The apparatus further has a chamber for receiving a material. The apparatus has an outlet. In use liquid volatilized by the heater passes, in the form of at least one of a vapor and an aerosol, through material received in the chamber to thereby entrain one or more constituents from the material to produce the inhalable medium which passes out of the outlet.

23 Claims, 2 Drawing Sheets

(51) Int. Cl.
  *A61M 11/04*   (2006.01)
  *A61M 15/00*   (2006.01)
  *F22B 1/28*    (2006.01)
  *H05B 3/44*    (2006.01)
  *A61M 21/00*   (2006.01)
  *A61M 16/10*   (2006.01)

(52) U.S. Cl.
  CPC ........ *A61M 15/0003* (2014.02); *A61M 15/06* (2013.01); *F22B 1/284* (2013.01); *H05B 3/44* (2013.01); *A61M 16/107* (2014.02); *A61M 2021/0016* (2013.01)

(56) References Cited

U.S. PATENT DOCUMENTS

| | | | |
|---|---|---|---|
| 5,027,836 | A | 7/1991 | Shannon |
| 5,027,839 | A | 7/1991 | Appell |
| 5,115,820 | A | 5/1992 | Hauser |
| 5,820,967 | A | 10/1998 | Gadkaree |
| 5,950,619 | A * | 9/1999 | van der Linden .......................... A61M 15/0065 128/200.14 |
| 6,814,786 | B1 | 11/2004 | Zhuang |
| 6,988,496 | B1 * | 1/2006 | Eicher ............... A61M 15/0065 128/200.14 |
| 7,160,366 | B2 | 1/2007 | Blackburn |
| 7,699,052 | B2 * | 4/2010 | Schiewe ........... A61M 15/0028 128/200.14 |
| 9,259,031 | B2 | 2/2016 | Branton |
| D761,998 | S | 7/2016 | Pinder |
| D768,915 | S | 10/2016 | Wright |
| D782,728 | S | 3/2017 | Pinder |
| D782,729 | S | 3/2017 | Wright |
| D805,684 | S | 12/2017 | Thuery |
| D815,342 | S | 4/2018 | Sutton |
| D818,635 | S | 5/2018 | Pinder |
| D818,638 | S | 5/2018 | Wright |
| D825,099 | S | 8/2018 | Wright |
| D825,103 | S | 8/2018 | Wright |
| 2004/0194792 | A1 | 10/2004 | Zhuang |
| 2005/0133051 | A1 | 6/2005 | Luan |
| 2005/0133054 | A1 | 6/2005 | Fournier |
| 2006/0144412 | A1 | 7/2006 | Mishra |
| 2006/0201524 | A1 | 9/2006 | Zhang |
| 2008/0092912 | A1 | 4/2008 | Robinson |
| 2008/0110470 | A1 | 5/2008 | Zhang |
| 2011/0226236 | A1 * | 9/2011 | Buchberger ......... A61M 11/041 128/200.23 |
| 2012/0318882 | A1 | 12/2012 | Abehasera |
| 2013/0192620 | A1 | 8/2013 | Tucker |
| 2013/0333700 | A1 | 12/2013 | Buchberger |
| 2014/0076340 | A1 | 3/2014 | Kizer et al. |
| 2014/0166029 | A1 | 6/2014 | Weigensberg |
| 2014/0261486 | A1 | 9/2014 | Potter |
| 2014/0299125 | A1 | 10/2014 | Buchberger |
| 2014/0305449 | A1 | 10/2014 | Plojoux |
| 2015/0027454 | A1 | 1/2015 | Li |
| 2015/0196059 | A1 | 7/2015 | Li |
| 2015/0257447 | A1 | 9/2015 | Sullivan |
| 2016/0120224 | A1 | 5/2016 | Mishra |
| 2016/0174610 | A1 | 6/2016 | Kuczaj |
| 2016/0255879 | A1 | 9/2016 | Paprocki |
| 2017/0143038 | A1 | 5/2017 | Dickens |
| 2017/0347706 | A1 * | 12/2017 | Aoun ..................... F22B 1/284 |
| 2018/0027882 | A1 | 2/2018 | Hepworth |
| 2018/0235276 | A1 * | 8/2018 | Zuleta .................. A24F 47/006 |
| 2018/0325174 | A1 * | 11/2018 | Sutton ..................... A24B 9/00 |

FOREIGN PATENT DOCUMENTS

| | | |
|---|---|---|
| CA | 2330782 | 7/2002 |
| CA | 2925645 A1 | 4/2015 |
| CN | 1054887 | 10/1991 |
| CN | 101433818 | 5/2009 |
| CN | 101557728 | 10/2009 |
| CN | 102834027 | 12/2012 |
| CN | 103315402 A | 9/2013 |
| CN | 103892467 | 7/2014 |
| CN | 204273243 U | 4/2015 |
| DE | 2940535 | 10/1980 |
| EP | 0 174 645 A2 | 3/1986 |
| EP | 0254551 | 1/1988 |
| EP | 0 307 118 | 8/1988 |
| EP | 0 352 106 A2 | 1/1990 |
| EP | 0 535 695 A2 | 4/1993 |
| EP | 0585016 | 3/1994 |
| EP | 0845220 | 6/1998 |
| EP | 1468618 | 10/2004 |
| EP | 2489391 A1 | 8/2012 |
| EP | 2 625 974 A1 | 8/2013 |
| EP | 3127443 | 2/2017 |
| JP | 06064983 | 3/1994 |
| JP | 2001-120250 | 5/2001 |
| JP | 2009191148 | 8/2009 |
| JP | 2010506594 | 3/2010 |
| JP | 2012506263 | 3/2012 |
| JP | 2014511175 | 5/2014 |
| JP | 2014 529996 A | 11/2014 |
| JP | 2015504667 | 2/2015 |
| JP | 2017-529896 | 10/2017 |
| KR | 20120053521 | 5/2012 |
| KR | 20140118982 | 10/2014 |
| WO | WO 98/28994 | 12/1997 |
| WO | WO 97048293 | 12/1997 |
| WO | WO 9748296 | 11/1998 |
| WO | WO 2001/030184 A1 | 5/2001 |
| WO | WO 03/008068 | 1/2003 |
| WO | WO 03/034847 A1 | 5/2003 |
| WO | WO 03056949 | 7/2003 |
| WO | WO 2004/086888 A1 | 10/2004 |
| WO | WO 2004/087309 A1 | 10/2004 |
| WO | WO 2006/048766 A1 | 5/2006 |
| WO | WO 2006/070291 A1 | 7/2006 |
| WO | WO 2006/072889 A1 | 7/2006 |
| WO | WO 2006/089404 A1 | 8/2006 |
| WO | WO 2006/097852 A1 | 9/2006 |
| WO | WO 2006/103404 A1 | 10/2006 |
| WO | WO 2006/109189 A1 | 10/2006 |
| WO | WO 2007/031876 A1 | 3/2007 |
| WO | WO 2007/036814 A1 | 4/2007 |
| WO | WO 2007/069093 A1 | 6/2007 |
| WO | WO 2008/108889 A1 | 9/2008 |
| WO | WO 2012/168699 A1 | 12/2012 |
| WO | WO 2013034458 | 3/2013 |
| WO | WO 2013/098405 A2 | 7/2013 |
| WO | WO 2013/102309 | 7/2013 |
| WO | WO 2013/120565 A2 | 8/2013 |
| WO | WO 2013/164705 A1 | 11/2013 |
| WO | WO 2014/116974 | 7/2014 |
| WO | WO 2014/116974 A1 | 7/2014 |
| WO | WO 2014/140320 A1 | 9/2014 |
| WO | WO 2015/046385 A1 | 4/2015 |
| WO | WO 2015/062983 A2 | 5/2015 |
| WO | WO 2015/128499 A1 | 9/2015 |
| WO | WO 2015/179388 A1 | 11/2015 |
| WO | WO 2016/062777 A1 | 4/2016 |

OTHER PUBLICATIONS

Australian Examination Report, Application No. 2015334902, dated May 15, 2018, 7 pages.
Korean Office Action, Application No. 10-2017-7013874, dated Apr. 25, 2018, 9 pages (16 pages with translation).
Canadian Office Action, Application No. 2,963,957, dated Mar. 16, 2018, 4 pages.
Application and File History for U.S. Appl. No. 15/553,785, filed Aug. 25, 2017, Inventor: Hepworth.
JAC Vapour E-Cigarettes & E-Liquids, Round Rubber Mouth Tips, www.jacapour.com , 2 pages, retrieved on Jan. 6, 2016.
International Preliminary Report on Patentability, International Application No. PCT/EP2016/054232, dated Jul. 3, 2017, 10 pages.

(56) References Cited

OTHER PUBLICATIONS

International Search Report, International Application No. PCT/EP2016/054232, dated Aug. 24, 2016, 5 pages.
GB Search Report, Application No. GB1517470.9, dated Mar. 21, 2016, 4 pages.
Partial International Search Report, International Application No. PCT/EP2016/054232, dated Jun. 22, 2016, 6 pages.
Application and File History for U.S. Appl. No. 15/553,742, filed Aug. 25, 2017, Inventor: Turner.
International Preliminary Report on Patentability, International Application No. PCT/EP2016/054159, dated Jul. 14, 2017, 7 pages.
International Search Report, International Application No. PCT/EP2016/054159, dated Jun. 9, 2016, 3 pages.
Application and File History for U.S. Appl. No. 15/307,074, filed Oct. 27, 2016, Inventor: England.
Definition of "throughout," the Free Merriam-Webster Dictionary, retrieved from the Internet on Mar. 7, 2015, available at: http://www.merriam-webster.com/dictionary/throughout.
International Search Report and Written Opinion, dated Sep. 17, 2012 for PCT/GB2012/051257, filed Jun. 1, 2012, 22 pages.
Written Opinion of the IPEA, dated May 29, 2013 for PCT/GB2012/051257, filed Jun. 1, 2012, 7 pages.
International Preliminary Report on Patentability, dated Jul. 12, 2013 for PCT/GB2012/051257, filed Jun. 1, 2012, 20 pages.
International Search Report for corresponding International Application No. PCT/GB2015/051253 dated Nov. 16, 2015; 6 pages.
Written Opinion for corresponding International Application No. PCT/GB2015/051253 dated Nov. 16, 2015; 7pages.
International Search Report, Application No. PCT/EP2015/074395, dated Feb. 1, 2016, 2 pages.
Chinese Office Action, Application No. 201580023549.5, dated Jul. 2, 2018, 23 pages.
Korean Office Action, Application No. 10-2017-7013874, dated Oct. 30, 2018, 9 pages (19 pages with translation).
European Communication, Application No. 15793718.6, dated Dec. 20, 2018, 5 pages.
Japanese Office Action, Application No. 2017-545230, dated Nov. 6, 2018, 10 pages.
Japanese Office Action, Application No. 2017-545245, dated Oct. 30, 2018, 11 pages.
Japanese Office Action, Application No. 2017-522122, dated Feb. 5, 2019, 7 pages.

* cited by examiner

INHALATOR AND CARTRIDGE THEREOF

CROSS-REFERENCE TO RELATED APPLICATIONS

The present application is a National Phase entry of PCT Application No. PCT/EP2015/074395, filed Oct. 21, 2015, which claims priority from GB Patent Application No. 1418817.1, filed Oct. 21, 2014, each of which is hereby fully incorporated herein by reference.

TECHNICAL FIELD

The present disclosure relates to apparatus for generating an inhalable medium and to a method of generating an inhalable medium, and a cartridge for use with an apparatus for generating an inhalable medium.

BACKGROUND

Smoking articles such as cigarettes, cigars and the like burn tobacco during use to create tobacco smoke. Attempts have been made to provide alternatives to these articles that burn tobacco by creating products that release compounds without burning. Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

According to a first aspect of the present disclosure, there is provided apparatus for generating an inhalable medium, the apparatus comprising: a container for holding a liquid; a heater for volatilizing liquid held in the container; a chamber for receiving a material; and an outlet; the arrangement being such that in use liquid volatilized by the heater passes, in the form of at least one of a vapor and an aerosol, through material received in the chamber to thereby entrain one or more constituents from the material to produce the inhalable medium which passes out of the outlet.

This allows the inhalable medium to have, for example, a flavor or flavors that are derived from the material contained in the apparatus in use. In a particular application, the vapor or aerosol passing over the material is hot and so heats the material to evaporate or volatilize one or more constituents from the material, allowing the constituents to be taken up into the inhalable medium.

As a particular non-limiting example, the material may be or include tobacco. One feature of so-called e-cigarette devices is that the flavor of the inhalable medium is often nothing like or at least is different from the flavor of a conventional tobacco product. In the case that the material in an embodiment of the present invention is or includes tobacco, the vapor or aerosol that passes over the tobacco picks up tobacco flavorings from the material.

In an embodiment, the heater for volatilizing liquid contained in the container is arranged to vaporize the liquid.

In an embodiment, the apparatus comprises a cooler or cooling zone downstream of the heater and upstream of the chamber, the cooler or cooling zone being arranged to cool vaporized liquid to form an aerosol of liquid droplets which in use passes through material received in the chamber. The cooler may be arranged in effect to act as a heat exchanger, allowing for recovery of heat from the vapor. The recovered heat can be used for example to pre-heat the material and/or to assist in heating the liquid.

In another embodiment, the heater for heating liquid contained in the container is arranged to heat the liquid to form an aerosol.

In an embodiment, the apparatus comprises a second heater for heating material received in the chamber. This enables the material to be heated by the heater, which encourages release of compounds from the material, and optionally allows a lower temperature to be used for the heated liquid.

In an embodiment, the chamber is removable from the apparatus. The chamber may be, for example, in the form of a cartridge or the like which contains the material. The whole chamber containing the material may in effect be a disposable item which is replaced as a whole after use. As an alternative, the arrangement may be such that the user removes the chamber from the apparatus, replaces used material in the chamber, and then places the chamber back in the apparatus.

In another embodiment, the chamber may be non-removable from the apparatus. In such an embodiment, the user may just replace the material after use.

In an embodiment, the liquid container is removable. The liquid container may be in the form of a pot or the like (which in some embodiments may be annular for example), and/or an absorbent wadding or the like. The whole liquid container containing the liquid may in effect be a disposable item which is replaced as a whole after use. As an alternative, the arrangement may be such that the user removes the liquid container from the apparatus, replaces used liquid or tops up liquid in the container, and then places the container back in the apparatus.

In another embodiment, the liquid container may be non-removable from the apparatus. In such an embodiment, the user may just replace used liquid or top up liquid in the container after use as necessary.

In an embodiment, the liquid container and the chamber are an integral unit.

In an embodiment, the chamber contains material, the material being in solid form. The material may be or comprise tobacco for example.

In an embodiment, the container holds liquid, the liquid containing nicotine.

In an embodiment, the container holds liquid, the liquid being or comprising glycerol.

In an embodiment, the container holds liquid, the liquid being or comprising flavorant.

In an embodiment, the apparatus is battery-operated.

In an embodiment, the or each heater is an electrically resistive heater.

According to a second aspect of the present disclosure, there is provided a method of generating an inhalable medium using an apparatus comprising a container holding a liquid, a heater for volatilizing the liquid, a material, and an outlet, the method comprising: volatilizing the liquid held in the container; entraining one or more constituents from the material in at least one of a vapor and an aerosol formed by the volatilized liquid by passing the at least one of a vapor and an aerosol through the material to generate the inhalable medium; and passing the inhalable medium out of the outlet.

In an embodiment, the volatilizing the liquid held in the container vaporizes at least a portion of the liquid. In an embodiment, the method comprises passing the vaporized liquid through a cooler or cooling zone of the apparatus to form an aerosol of liquid droplets which passes through the material.

In an embodiment, the volatilizing the liquid contained in the container volatilizes the liquid to form an aerosol.

In an embodiment, the method comprises heating the material using a second heater of the apparatus.

In an embodiment, the material is contained in the apparatus in solid form. The material may be or may comprise tobacco.

In an embodiment, the liquid contains nicotine.

In an embodiment, the liquid is or comprises glycerol.

In an embodiment, the liquid is or comprises a flavorant.

According to a third aspect of the present disclosure, there is provided a cartridge for use with an apparatus for generating an inhalable medium, the cartridge comprising: a container for holding a liquid; a receptacle for receiving a solid material; the cartridge being arranged such that vaporized liquid exiting the container can flow, in the form of at least one of a vapor and an aerosol, through solid material received by the receptacle in use.

In an embodiment, the cartridge comprises a heater associated with the container for volatizing a liquid held in the container in use.

In an embodiment, the cartridge comprises a heater associated with the receptacle for heating a solid material received by the receptacle in use.

BRIEF DESCRIPTION OF THE DRAWINGS

Embodiments of the disclosure will now be described, by way of example only, with reference to the accompanying drawings, in which.

DETAILED DESCRIPTION

Figure 1:
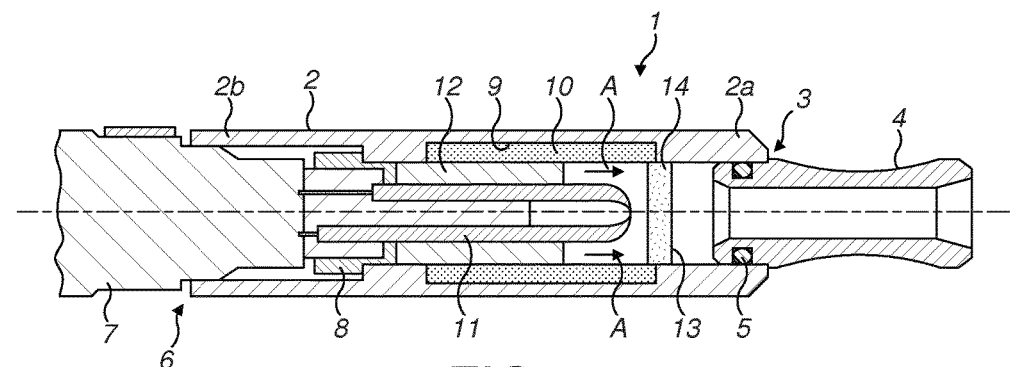
FIG. 1 shows a schematic longitudinal cross-sectional view of an example of an apparatus for generating an inhalable medium.

Referring to FIG. 1, there is shown an example of an apparatus 1 for generating an inhalable medium. In broad outline, the apparatus 1 volatilizes a liquid to form a vapor or an aerosol which passes through a material so as to produce an inhalable medium that contains one or more constituents derived from the material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Returning to FIG. 1, the apparatus 1 of this example has a generally hollow cylindrical outer housing 2. The housing 2 has an open end 3. In this example, a tubular mouthpiece 4 is provided in the open end 3. The mouthpiece 4 in this example is removable by a user from the housing 2. An O-ring or other seal 5 assists in sealing the mouthpiece 4 in the housing 2. At or towards the other end 6 of the housing 2 is a battery 7 for powering various components of the apparatus 1, as will be discussed further below. The battery 7 may be a rechargeable battery or a disposable battery. A controller 8 is also provided in the housing 2 for controlling the operation of various components of the apparatus 1, as will be discussed further below.

The housing 2 has a container 9 for holding or containing a liquid 10. Various different forms for the container 9 may be used. In the example of FIG. 1, the container 9 is in the form of an annular chamber 9 provided in the housing 2 between the open end 3 and the other end 6. In this particular example, the housing 2 is in two parts, a first part 2a being towards the open end 3 and a second part 2b towards the other end 6. The first and second parts 2a,2b of the housing 2 may connect to each other via a screw thread, a bayonet fitting or the like. In use, a user can separate the first and second parts 2a, 2b of the housing 2 to allow the liquid 10 to be replenished or replaced as necessary. Alternatively, the mouthpiece 4 can be removed to provide access to the container 9. It will be understood however that other arrangements are possible. For example, the liquid 10 may be provided in a discrete annular pot-like container which can be removed as a whole from the housing 2. Such a discrete container may be disposable so that the user replaces the liquid 10 by fitting a new container with liquid 10 in the housing 2. Alternatively, such a container may be reusable. In such a case, the user may replenish or replace liquid 10 in the container whilst it has been removed from the housing 2 and then replace the refilled container in the housing 2. It will be understood that the housing 2 need not be in two parts and that other arrangements enabling access for the user may be provided, for example, to enable refilling in situ.

A heater 11 is provided generally centrally of the housing 2, that is, centrally along the length and width of the housing 2 in this example. In this example, the heater 11 is powered by the battery 7 and is therefore electrically connected to the battery 7. The heater 11 may be an electrically resistive heater, including for example a nichrome resistive heater, a ceramic heater, etc. The heater 11 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used, including non-electrical heating arrangements.

This heater 11 is provided for volatilizing the liquid 10. In the example shown, an annular wick 12 surrounds the heater 11 and is in (thermal) contact with the heater 11. The outermost surface of the annular wick 12 is in contact with liquid 10 contained in the liquid container 9. The wick 12 is generally absorbent and acts to draw in liquid 10 from the liquid container 9 by capillary action. In some embodiments, the wick 12 is non-woven and may be for example a cotton or wool material or the like, or a synthetic material, including for example polyester, nylon, viscose, polypropylene or the like. Whilst this will be described more fully below, it may be noted here that in use, liquid 10 drawn into the wick 12 is heated by the heater 11. The liquid 10 may be volatilized so as to produce an aerosol of liquid droplets or sufficiently heated to produce a vapor. The aerosol or vapor so produced exits the wick 12 and passes towards the mouthpiece 4 as shown by the arrows A under the action of the user drawing on the mouthpiece 4. The heater 11 and wick 12 may be provided as a single, effectively integral item such that the heating and wicking is effectively carried out by a single unit.

The housing 2 further contains a chamber 13 which holds or contains a material 14 in the apparatus 1. In use, a user can access the chamber 13 to replace or replenish the material 14 through the open end 3 of the housing 2 by removing the mouthpiece 4 and/or by separating the two parts 2a,2b of the housing 2. Various different forms for the chamber 13 may be used. For example, the chamber 13 may be a tube which is completely open at both ends and which contains the material 14. As another example, the chamber 13 may be a tube which has one or more end walls which have through holes through which a vapor or aerosol can pass. The chamber 13 may remain in situ within the housing 2 whilst the user removes and replaces the material 14. Alternatively, the chamber 13 containing the material may be a discrete item which in use is inserted into and removed from the housing 2 as a whole. A removable chamber 13 of this type may be disposable so that the user replaces the material 14 by fitting a new chamber 13 containing fresh material 14 into the housing 2. As an alternative, the chamber 13 may be reusable. In such a case, the user may replace the material 14 in the chamber 13 whilst the chamber 13 has been removed from the housing 2 and then replace the refilled chamber 13 in the housing 2. In yet another example, the chamber 13 may comprise clips or the like provided internally of the housing 2 and which retain the material 14 in position. In some examples, the material 14 could simply fit snugly within the chamber 13. As another alternative, the container 9 for containing the liquid 10 may itself be arranged to support or carry the material 14. For example, the container 9 may have one or more clips or a tube or the like for receiving and holding the material 14 in position. Such a dual function container 9/chamber or receptacle 13 for both containing the liquid 10 and receiving the material 14 may be in the form of a cartridge or the like and may be a disposable item or may be re-useable, with the liquid 10 and material 14 being replaced or topped up by the user as required. In some cases, it may be that the user only needs to top up or replace the material 14 from time to time, with sufficient liquid 10 being provided for several uses. Once the liquid 10 has been consumed, the user disposes of the dual function container 9/receptacle 13 and uses a new one. Likewise, it may be that the user only needs to top up or replace the liquid 10 from time to time, with sufficient material 14 being provided for several uses. Once the material 14 has been consumed, the user disposes of the dual function container 9/receptacle 13 and uses a new one.

The material 14 is located in the housing 2 downstream of the location where the aerosol or vapor is produced from the liquid 10 and upstream of the open end 3 of the housing 2 and the mouthpiece 4. In this particular example, the material 14 is effectively provided in the same portion or chamber of the housing 2 as the wick 12. The aerosol or vapor produced from the liquid 10 exits the wick 12 and passes as shown by the arrows A towards the material 14 under the action of the user drawing on the mouthpiece 4. In particular embodiments, the material 14 is porous so that the aerosol or vapor passes through the material 14 and then through the open end 3 of the housing 2 and the mouthpiece 4. In some embodiments, the material 14 and/or its chamber 13 are arranged so that there is no air gap between the material 14/chamber 13 and the interior of the housing 2 so that the aerosol or vapor flows entirely through the material 14.

In some embodiments, the liquid 10 is a liquid that is volatilizable at reasonable temperatures, such as in the range of 150-250° C., as that helps to keep down the power consumption of the apparatus 1. Suitable materials include those conventionally used in e-cigarette devices, including for example propylene glycol and glycerol (also known as glycerine).

The material 14 is a material that may be used to impart a flavor to the aerosol or vapor produced from the liquid 10 as the aerosol or vapor passes through the material 14. The material 14 may for example consist of or comprise tobacco. As the aerosol or vapor passes through and over the tobacco material 14, the hot aerosol or vapor entrains organic and other compounds or constituents from the tobacco material 14 that lend tobacco its organoleptic properties, thus imparting the flavor to the aerosol or vapor as it passes to the mouthpiece 4. It will be understood however that materials other than tobacco may be used to impart different flavors to the aerosol or vapor stream. For example, flavorants could be included in the material or in the liquid.

In addition, where the material 14 is or includes tobacco, it may be that the aerosol or vapor stream draws sufficient nicotine from the tobacco material 14. Alternatively or additionally, where the material 14 does not contain any tobacco, the material 14 may be enhanced with nicotine, for example by coating the material with nicotine. Indeed, even in the case that the material 14 is or includes tobacco, the material 14 may be coated or otherwise enhanced with nicotine. As another example, whether or not the material 14 is or includes tobacco and/or includes nicotine, nicotine may be provided in the liquid 10. Accordingly, where it is intended that the apparatus 1 provides nicotine for the user, the nicotine may be provided in the liquid 10, may be obtained from the material 14 in the case that the material is or includes tobacco, may be provided as a coating or the like on non-tobacco material 14, may be provided as a coating or the like on tobacco material, or any combination of these. Likewise, flavorings may be added to the material 14 (whether or not the material is or includes tobacco) and/or to the liquid 10.

As mentioned above, heating devices are known that release compounds by heating, but not burning, tobacco. It may be noted here that tobacco is a poor heat conductor, and yet the heating of tobacco in known tobacco heating devices is by heat conduction through the tobacco from an exterior surface of the tobacco (typically by virtue of an electrical resistive heating element which is in contact with the surface of the tobacco). This means that the tobacco may be heated inefficiently and/or the power consumption of the device is high. In the case of a battery-operated device, high power consumption is a problem for the user as the battery or batteries need to be recharged or replaced frequently. In the case that the material 14 is tobacco, this can be avoided in embodiments of the present apparatus 1 as the material 14 can be heated by the hot aerosol or vapor passing through the body of the porous tobacco material 14, providing for more effective and efficient heating throughout the body of the tobacco material 14. This can help to lower the power consumption of the apparatus 1.

In the example shown in FIG. 1, the only heat source for heating the material 14 in the apparatus 1, which is required so as to generate the organic and other compounds or constituents from the material 14, is the hot aerosol or vapor produced from heating the liquid 10.

Figure 2:
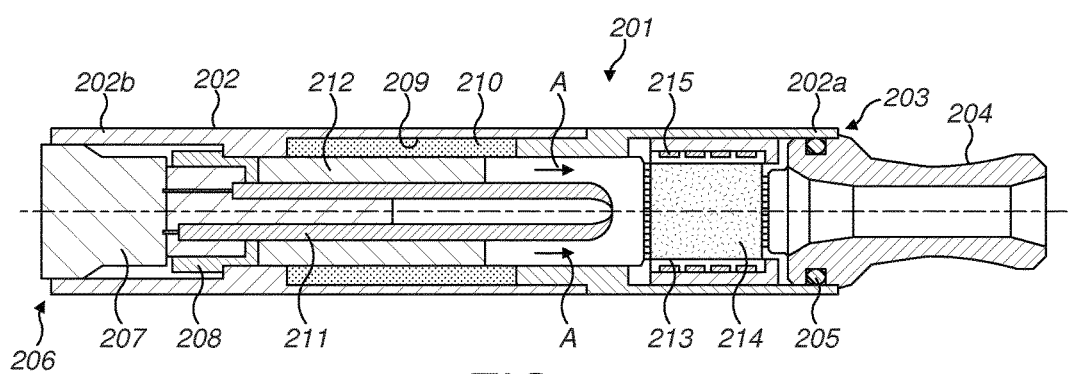
FIG. 2 shows a schematic longitudinal cross-sectional view of another example of an apparatus for generating an inhalable medium.

Referring now to FIG. 2, there is shown another example of an apparatus for generating an inhalable medium. In the following description and in FIG. 2, components and features that are the same as or similar to the corresponding components and features of the example described with reference to FIG. 1 have the same reference numeral but increased by 200. For the sake of brevity, the description of those components and features will not be repeated in its entirety here. It will be understood that the arrangements and alternatives, etc., described above in relation to the example of FIG. 1 are also applicable to the example of FIG. 2. Again, in broad outline, the apparatus 201 of FIG. 2 heats a liquid to form a vapor or an aerosol which passes through a material 214 so as to produce an inhalable medium that contains one or more constituents derived from the material 214.

The apparatus 201 of this example has a generally hollow cylindrical outer housing 202 with an open end 203 and a tubular mouthpiece 204. The mouthpiece 204 in this example is removable by a user from the housing 202 and an O-ring or other seal 205 assists in sealing the mouthpiece 204 in the housing 202. A battery 207 for powering various components of the apparatus 201 and a controller 208 are provided at or towards the other end 206 of the housing 202. The housing 202 of this example is in two parts, a first part 202a being towards the open end 203 and a second part 202b towards the other end 206.

The housing 202 has a container 209 for holding or containing a liquid 210. The container 209 may be of any of the types described above in relation to the example of FIG. 1. A heater 211 is provided generally centrally (lengthwise and widthwise) of the housing 202 for volatilizing the liquid 210. In this example, the heater 211 is powered by the battery 207 and is therefore electrically connected to the battery 207. The heater 211 may be an electrically resistive heater, a ceramic heater, etc. The heater 211 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used, including non-electrical heating arrangements. An annular wick 212 surrounds the heater 211 and is in (thermal) contact with the heater 211. The outermost surface of the annular wick 212 is in contact with liquid 210 contained in the liquid container 209. The liquid 210 may be heated so as to produce an aerosol of liquid droplets or sufficiently heated to produce a vapor. The aerosol or vapor so produced exits the wick 212 and passes towards the mouthpiece 204 as shown by the arrows A under the action of the user drawing on the mouthpiece 204. The heater 211 and wick 212 may be provided as a single, effectively integral item such that the heating and wicking is effectively carried out by a single unit.

The housing 202 further contains a chamber 213 which holds or contains a material 214 in the apparatus 201. The chamber 213 may be of any of the types described above in relation to the example of FIG. 1. The material 214 is located in the housing 202 downstream of the location where the aerosol or vapor is produced from the liquid 210 and upstream of the open end 203 of the housing 202 and the mouthpiece 204. In this particular example, the material 214 is effectively provided in the same portion or chamber of the housing 202 as the wick 212. The aerosol or vapor produced from the liquid 210 exits the wick 212 and passes as shown by the arrows A towards the material 214 under the action of the user drawing on the mouthpiece 204. In particular embodiments, the material 214 is porous so that the aerosol or vapor passes through the material 214 and then through the open end 203 of the housing 202 and the mouthpiece 204. In some embodiments, the material 214 and/or its chamber 213 are arranged so that there is no air gap between the material 214/chamber 213 and the interior of the housing 202 so that the aerosol or vapor flows entirely through the material 214. As above, the material 214 is a material that may be used to impart a flavor to the aerosol or vapor produced from the liquid 210 as the aerosol or vapor passes through the material 214. The material 214 may for example consist of or comprise tobacco. As the aerosol or vapor passes through and over the tobacco material 214, the hot aerosol or vapor entrains organic and other compounds or constituents from the tobacco material 214 that lend tobacco its organoleptic properties, thus imparting the flavor to the aerosol or vapor as is passes to the mouthpiece 204. It will be understood however that materials other than tobacco may be used to impart different flavors to the aerosol or vapor stream. The container 209 for containing the liquid 210 may itself be arranged to support or carry the material 214. For example, the container 209 may have one or more clips or a tube or the like for receiving and holding the material 214 in position. Such a dual function container 209/chamber or receptacle 213 for both containing the liquid 210 and receiving the material 214 may be in the form of a cartridge or the like and may be a disposable item or may be re-useable, with the liquid 210 and material 214 being replaced or topped up by the user as required. In some cases, it may be that the user only needs to top up or replace the material 214 from time to time, with sufficient liquid 210 being provided for several uses. Once the liquid 210 has been consumed, the user disposes of the dual function container 209/receptacle 213 and uses a new one. Likewise, it may be that the user only needs to top up or replace the liquid 210 from time to time, with sufficient material 214 being provided for several uses. Once the material 214 has been consumed, the user disposes of the dual function container 209/receptacle 213 and uses a new one.

In the example apparatus 201 of FIG. 2, a second heater 215, such as an oven heater, is provided in thermal contact with the material 214 to pre-heat the material 214 and/or provide additional heat to the material 214 throughout use of the apparatus 201. This encourages release of constituents from the material 214 as the vapor or aerosol passes through the material 214 in use. This also optionally allows a lower temperature to be used for the heated liquid 210, which reduces the power consumption of the first heater 211 which heats the liquid 210, and also may allow the amount of heated liquid 210 that has to be used to achieve sufficient heating of the material 214 to be reduced. The second heater 215 may be an electrically resistive heater, a ceramic heater, etc., powered by for example the battery 207. The second heater 215 may be for example a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. Other heating arrangements may be used for the second heater 215, including non-electrical heating arrangements.

In the example apparatus 201 of FIG. 2, the heater 215 for heating the material 214 is provided externally of the material 214 and heats the material 214 by heat conduction from the exterior of the material 214. The heater 215 in this example is generally cylindrical. The heater 215 may in effect be an integral part of the apparatus 201 and be provided as part of the housing 202. As an alternative, the heater 215 may be provided integrally with the chamber 213 which holds or contains the material 214. In this alternative, in the case that the chamber 213 is disposable, the heater 215 will be replaced when a new chamber 213 with fresh material is loaded into the apparatus 201 by the user.

Figure 3:
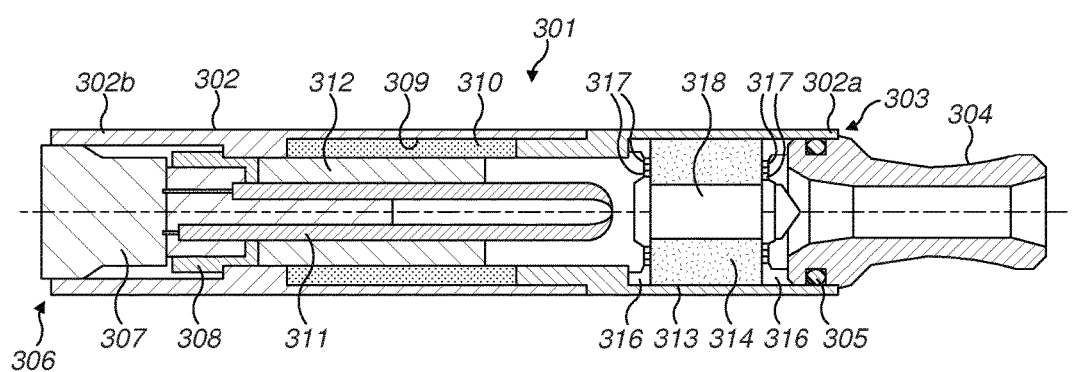
FIG. 3 shows a schematic longitudinal cross-sectional view of another example of an apparatus for generating an inhalable medium.

Referring now to FIG. 3, there is shown another example of an apparatus for generating an inhalable medium. In the following description and in FIG. 3, components and features that are the same as or similar to the corresponding components and features of the example described with reference to FIG. 1 have the same reference numeral but increased by 300. For the sake of brevity, the description of those components and features will not be repeated in its entirety here. It will be understood that the arrangements and alternatives, etc. described above in relation to the examples of FIG. 1 and FIG. 2 are also applicable to the example of FIG. 3. Again, in broad outline, the apparatus 301 of FIG. 3 heats a liquid to form a vapor or an aerosol which passes through a material 314 so as to produce an inhalable medium that contains one or more constituents derived from the material 314.

The apparatus 301 of this example again has a generally hollow cylindrical outer housing 302 with an open end 303 and a tubular mouthpiece 304, which is removable by a user from the housing 302. O-ring or other seal 305 assists in sealing the mouthpiece 304 in the housing 302. A battery 307 for powering various components of the apparatus 301 and a controller 308 are provided at or towards the other end 306 of the housing 302. The housing 302 of this example is again in two parts, a first part 302a being towards the open end 303 and a second part 302b towards the other end 306.

The housing 302 has a container 309 for holding or containing a liquid 310. The container 309 may be of any of the types described above in relation to the examples of FIGS. 1 and 2. A heater 311 is provided generally centrally of the housing 302 for heating the liquid 310. The heater 311 may be any of the types described above. In this example, the heater 311 is powered by the battery 307 and is therefore electrically connected to the battery 307. An annular wick 312 surrounds the heater 311 and is in (thermal) contact with the heater 311. The outermost surface of the annular wick 312 is in contact with liquid 310 contained in the liquid container 309. The liquid 310 may be heated so as to produce an aerosol of liquid droplets or sufficiently heated to produce a vapor. The aerosol or vapor so produced exits the wick 312 and passes towards the mouthpiece 304 as shown by the arrows A under the action of the user drawing on the mouthpiece 304. The heater 311 and wick 312 may be provided as a single, effectively integral item such that the heating and wicking is effectively carried out by a single unit.

The housing 302 further contains a chamber 313 which holds or contains a material 314 in the apparatus 301. The chamber 313 may be of any of the types described above in relation to the examples of FIGS. 1 and 2. (In the example shown in FIG. 3, the chamber 313 is in the form of a tube which has end walls 316 which have through holes 317 through which a vapor or aerosol can pass, which was mentioned as an option above.) The material 314 is located in the housing 302 downstream of the location where the aerosol or vapor is produced from the liquid 310 and upstream of the open end 303 of the housing 302 and the mouthpiece 304. In this particular example, again, the material 314 is effectively provided in the same portion or chamber of the housing 302 as the wick 312. The aerosol or vapor produced from the liquid 310 exits the wick 312 and passes as shown by the arrows A towards the material 314 under the action of the user drawing on the mouthpiece 304. In particular embodiments, the material 314 is porous so that the aerosol or vapor passes through the material 314 and then through the open end 303 of the housing 302 and the mouthpiece 304. In some embodiments, the material 314 and/or its chamber 313 are arranged so that there is no air gap between the material 314/chamber 313 and the interior of the housing 302 so that the aerosol or vapor flows entirely through the material 314. As above, the material 314 is a material that may be used to impart a flavor to the aerosol or vapor produced from the liquid 310 as the aerosol or vapor passes through the material 314. The material 314 may for example consist of or comprise tobacco. As the aerosol or vapor passes through and over the tobacco material 314, the hot aerosol or vapor entrains organic and other compounds or constituents from the tobacco material 314, thus imparting tobacco flavor to the aerosol or vapor as is passes to the mouthpiece 304. It will be understood, however, that materials other than tobacco may be used to impart different flavors to the aerosol or vapor stream. The container 309 for containing the liquid 310 may itself be arranged to support or carry the material 314. For example, the container 309 may have one or more clips or a tube or the like for receiving and holding the material 314 in position. Such a dual function container 309/chamber or receptacle 313 for both containing the liquid 310 and receiving the material 314 may be in the form of a cartridge or the like and may be a disposable item or may be reusable, with the liquid 310 and material 314 being replaced or topped up by the user as required. In some cases, it may be that the user only needs to top up or replace the material 314 from time to time, with sufficient liquid 310 being provided for several uses. Once the liquid 310 has been consumed, the user disposes of the dual function container 309/receptacle 313 and uses a new one. Likewise, it may be that the user only needs to top up or replace the liquid 310 from time to time, with sufficient material 314 being provided for several uses. Once the material 314 has been consumed, the user disposes of the dual function container 309/receptacle 313 and uses a new one.

In the example apparatus 301 of FIG. 3, a second heater 318 is again provided in thermal contact with the material 314 to heat the material 314 to encourage release of constituents from the material 314 as the vapor or aerosol passes through the material 314 in use. The second heater 318 may be an electrically resistive heater, a ceramic heater, etc., powered by for example the battery 307. Other heating arrangements may be used for the second heater 318, including non-electrical heating arrangements.

In the example apparatus 301 of FIG. 3, the heater 318 for heating the material 314 is provided internally of the material 314 and heats the material 314 by heat conduction from the interior of the material 314. The heater 318 in this example is generally in the form of a cylindrical rod located along the central longitudinal axis of the material 314. In other arrangements, the heater 318 may be a wire, which may for example be in the form of a coil, a plate (which may be a multi-layer plate of two or more different materials, one or more of which may be electrically conductive and one or more of which may be electrically non-conductive), a mesh (which may be woven or non-woven for example, and which again may be similarly multi-layer), a film heater, etc. The material 314 in this case is generally tubular or otherwise has an internal aperture for receiving the heater 318. The heater 318 may in effect be an integral part of the apparatus 301 and be provided as part of the housing 302. In this case, as the material 314 is loaded into the apparatus 301 (for example, as the chamber 313 containing the material 314 is loaded into the apparatus 301), the material 314 surrounds the second heater 318. As an alternative, the heater 318 may be provided integrally with the chamber 313 which holds or contains the material 314. In this alternative, in the case that the chamber 313 is disposable, the heater 318 will be replaced when a new chamber 313 with fresh material is loaded into the apparatus 301 by the user.

In another example, plural internal heaters 318 may be provided, so as to provide for more efficient heating of the material 314. In another example, the material 314 may be heated by both one or more external heaters (like the second heater 215 of the example of FIG. 2) and by one or more internal heaters 314 (like the second heater 318 of the example of FIG. 3).

Figure 4:
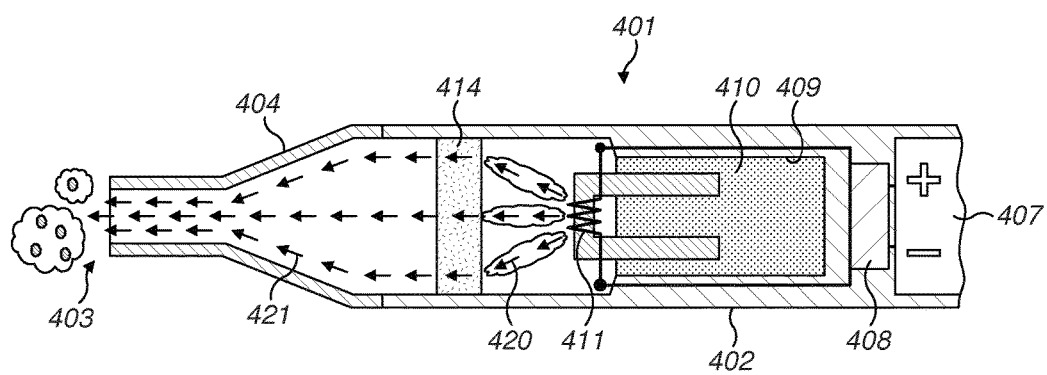
FIG. 4 shows a schematic longitudinal cross-sectional view of an example of an apparatus for generating an inhalable medium in use.

Referring now to FIG. 4, there is shown a schematic longitudinal cross-sectional view of an example of an apparatus 401 for generating an inhalable medium in use. Again, for the sake of brevity, a detailed description of the components and features that are the same as or similar to the corresponding components and features of the examples described will not be given here. Reference numerals for those components and features of the example described with reference to FIG. 1 have the same reference numeral but increased by 400. It will be understood that the arrangements and alternatives, etc., described are also applicable to the example of FIG. 4.

In this example, the liquid 410 is heated to form a vapor 420. Under the action of the user drawing on the mouthpiece 404/open end 403 of the housing 402, the vapor 420 is drawn through the material 414. The vapor 420, which is hot, entrains organic and other compounds or constituents from the material 414. Depending on for example the temperatures used, the vapor 420 may condense to form an aerosol of droplets as heat is transferred from the vapor 420 to the material 414. The compounds or constituents evaporated from the material 414 may condense on the aerosol droplets. Thus, the vapor or aerosol 421 that passes to the mouthpiece 404/open end 403 of the housing 402 picks up the flavor from the material 414. In the case that the material 414 contains or includes nicotine, the vapor or aerosol 421 that passes to the mouthpiece 404/open end 403 of the housing 402 also contains nicotine entrained from the material 414.

Figure 5:
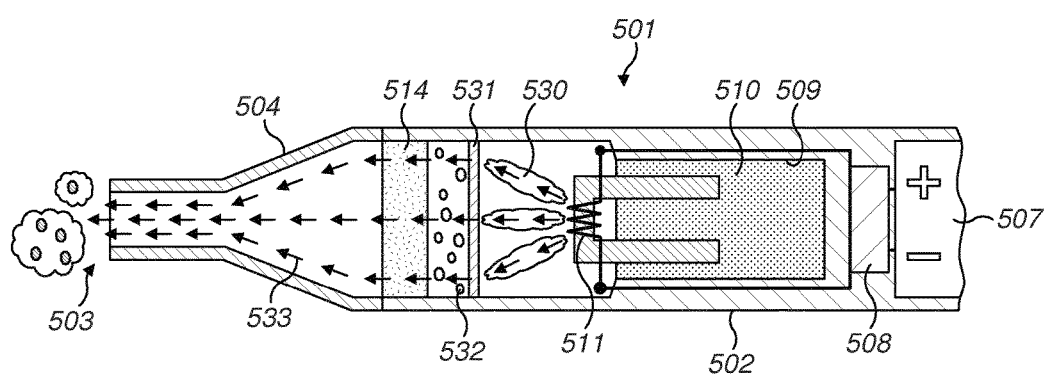
FIG. 5 shows a schematic longitudinal cross-sectional view of another example of an apparatus for generating an inhalable medium in use.

Referring now to FIG. 5, there is shown a schematic longitudinal cross-sectional view of another example of an apparatus 501 for generating an inhalable medium in use. Again, for the sake of brevity, a detailed description of the components and features that are the same as or similar to the corresponding components and features of the examples described will not be given here. Reference numerals for those components and features of the example described with reference to FIG. 4 have the same reference numeral but increased by 100. It will be understood that the arrangements and alternatives, etc., described are also applicable to the example of FIG. 5.

In this example, again the liquid 510 is heated to form a vapor 530. Under the action of the user drawing on the mouthpiece 504/open end 503 of the housing 502, the vapor 530 is drawn towards the material 514. In this example, the vapor 530 passes through a cooler or heat exchanger 531. This causes the vapor 530 to condense to form an aerosol 532 of droplets. The aerosol 532 then passes through the material 514 and, being hot, entrains organic and other compounds or constituents from the material 514, with the compounds condensing on the aerosol droplets. Moreover, especially in the case that the material 514 contains water, it may be that the mixture of the water evaporated from the material 514 and the droplets of liquid 510 vaporizes (rather than being an aerosol) owing to the relatively lower boiling point of the mixture. Thus, the vapor or aerosol 533 that passes to the mouthpiece 504/open end 503 of the housing 502 picks up the flavor from the material 514. In the case that the material 514 contains or includes nicotine, the vapor or aerosol 533 that passes to the mouthpiece 504/open end 503 of the housing 502 also contains nicotine entrained from the material 514.

In any of the examples described above, the controller (8 in FIG. 1, 208 in FIG. 2, etc.) controls operation of the apparatus 1 as a whole. The controller for example may cause the various heating elements to be powered as and when required and switch off the various heating elements when heating is not required. Operation of the one or more heating elements may be controlled so that the liquid and/or material is heated to an optimum temperature. Particular considerations include ensuring that the material does not burn, ensuring that adequate vaporization of the liquid is achieved, ensuring that the vaporized liquid or aerosol is at an appropriate temperature to liberate compounds from the material, and ensuring that the vapor or aerosol that reaches the user is at a comfortable and safe temperature. Where there are separate heaters for the liquid and for the material, the control may be arranged so that only the liquid is heated, only the material is heated, or both the liquid and the material are heated, optionally under user control. A puff detector, a device which is known per se, may be provided to signal to the controller when the one or more heating elements need to be energized. The apparatus may also have one or more filters for filtering the vapor or aerosol before it reaches the user, cooling arrangements for cooling the vapor or aerosol before it reaches the user, insulation internally of the apparatus to protect the user from the heat generated inside the housing, etc.

In use, and particularly in the case that the material 14, 214, etc. is tobacco, the tobacco, or at least the surface of the tobacco, can be heated to a temperature of between around 190° C. to 210° C., such as around 200° C., so as to ensure that an adequate or appropriate amount of the compounds are released from the tobacco. As described in more detail above, the material 14 may be heated only by the hot vapor or aerosol that passes through the material or the material may also be pre-heated or dual-heated using for example a dedicated heater. In the case of pre-heating, the material, particularly in the case of tobacco, may be pre-heated to a temperature in the range of around 100 to 150° C. It will be appreciated however that other temperatures may be used. For example, the material, or at least the surface of the material, may be heated to a temperature above 210° C., such as up to around 230° C. or 240° C. or so and even as high as 290° C. or so. The amount of tobacco present may be for example in the range 50 to 300 mg or so. In a typical example, the amount of tobacco that is heated per operation of the apparatus 1 (i.e. per puff) may be in the corresponding range of around 8 to 50 mg. A most suitable value for the amount of tobacco may be for example in the range 50 to 110 mg or so.

In use, the liquid 10, 210, etc., may be heated to a temperature of between around 150° C. to 250° C.

Suitable materials 14, etc., include materials that provide volatilized components upon heating, typically in the form of an aerosol. Suitable materials 14, etc., include any tobacco-containing material and may, for example, include one or more of tobacco per se, tobacco derivatives, expanded tobacco, reconstituted tobacco, ground tobacco, tobacco extract, homogenized tobacco or tobacco substitutes. In the case of tobacco, the material 14, etc. may be in the form of a rod of tobacco, a pod or plug of tobacco, loose tobacco, agglomerates, etc., and may be in relatively dry form or in relatively moist form for example. Suitable materials 14, etc., may include other, non-tobacco, products, which, depending on the product, may or may not contain nicotine.

As used herein, the terms "flavor" and "flavorant" refer to materials which, where local regulations permit, may be used to create a desired taste or aroma in a product for adult consumers.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus *Mentha*), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In order to address various issues and advance the art, the entirety of this disclosure shows by way of illustration and example various embodiments in which the claimed invention may be practiced and which provide for a superior apparatus arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. Apparatus for generating an inhalable medium, the apparatus comprising:
    a container for holding a liquid;
    a wick for drawing the liquid from the container;
    a heater for volatilizing the liquid drawn into the wick from the container;
    a chamber for receiving a material; and
    an outlet;
    wherein, in use, liquid volatilized by the heater passes, in the form of at least one of a vapor or an aerosol, through the material received in the chamber to thereby entrain one or more constituents from the material to produce the inhalable medium which passes out of the outlet, and wherein the wick is a cotton material.

2. Apparatus according to claim 1, wherein the heater for volatilizing the liquid drawn into the wick from the container is arranged to vaporize the liquid.

3. Apparatus according to claim 2, comprising a cooler or cooling zone downstream of the heater and upstream of the chamber, the cooler or cooling zone being arranged to cool vaporized liquid to form an aerosol of liquid droplets which in use passes through the material received in the chamber.

4. Apparatus according to claim 1, wherein the heater for volatilizing the liquid drawn into the wick from the container is arranged to heat the liquid to form an aerosol.

5. Apparatus according to claim 1, comprising a second heater for heating the material received in the chamber.

6. Apparatus according to claim 1, wherein the chamber is removable from the apparatus.

7. Apparatus according to claim 1, wherein the chamber is non-removable from the apparatus.

8. Apparatus according to claim 1, wherein the liquid container is removable.

9. Apparatus according to claim 1, wherein the liquid container and the chamber are an integral unit.

10. Apparatus according to claim 1, wherein the chamber contains the material, the material being in solid form.

11. Apparatus according to claim 1, wherein the material is or comprises tobacco.

12. Apparatus according to claim 1, wherein the container contains a flavorant and the liquid, the liquid comprising at least one of nicotine or glycerol.

13. Apparatus according to claim 1, wherein at least one of: the apparatus is battery-operated, or the or each heater is an electrically resistive heater.

14. Apparatus according to claim 1, wherein the cotton material is a non-woven cotton material.

15. A method of generating an inhalable medium using an apparatus comprising a container holding a liquid, a wick for drawing the liquid from the container, the wick being a cotton material, a heater for volatilizing the liquid drawn into the wick from the container, a material, and an outlet, the method comprising:
    volatilizing the liquid drawn into the wick from the container;
    entraining one or more constituents from the material in at least one of a vapor or an aerosol formed by the volatilized liquid by passing the at least one of a vapor or an aerosol through the material to generate the inhalable medium; and
    passing the inhalable medium out of the outlet.

16. A method according to claim 15, wherein the cotton material is a non-woven cotton material.

17. A cartridge for use with an apparatus for generating an inhalable medium, the cartridge comprising:
    a container for holding a liquid;
    a wick for drawing the liquid from the container for volatilizing by a heater in use; and
    a receptacle for receiving a solid material;
    the cartridge being arranged such that volatilized liquid exiting the container can flow, in the form of at least one of a vapor or an aerosol, through the solid material received by the receptacle in use,
wherein the wick is a cotton material.

18. A cartridge according to claim 17, comprising at least one of: a heater associated with the container for volatilizing the liquid in use, or a heater associated with the receptacle for heating a solid material received by the receptacle in use.

19. A cartridge according to claim 17, wherein the container has one or more apertures to allow volatilized liquid to exit the container.

20. A cartridge according to claim 17, wherein the receptacle contains the solid material.

21. A cartridge according to claim 20, wherein the material is or comprises tobacco.

22. A cartridge according to claim 17, wherein the receptacle comprises a chamber.

23. A cartridge according to claim 17, wherein the cotton material is a non-woven cotton material.

\* \* \* \* \*